United States Patent [19]

Hennessy et al.

[11] 4,063,309
[45] Dec. 13, 1977

[54] MEAN CORPUSCULAR VOLUME MEASURING APPARATUS AND METHOD

[75] Inventors: James William Hennessy, Trumbull; Bruce Munson Turner, Brandford, both of Conn.

[73] Assignee: Hycel, Inc., Houston, Tex.

[21] Appl. No.: 723,805

[22] Filed: Sept. 16, 1976

[51] Int. Cl.² .................. G06F 15/36; G06M 11/04
[52] U.S. Cl. ................... 364/555; 324/71 CP; 235/92 PC; 364/416
[58] Field of Search ........... 235/151.3, 151.35, 92 PC; 324/71 CP

[56] References Cited

U.S. PATENT DOCUMENTS

| 3,626,164 | 12/1971 | Pontigny et al. | 235/151.3 |
| 3,686,486 | 8/1972 | Coulter et al. | 235/151.3 |
| 3,699,319 | 10/1972 | Berg | 235/151.34 |
| 3,828,260 | 8/1974 | Underwood | 235/151.35 X |
| 3,973,189 | 8/1976 | Angel et al. | 235/151.3 X |
| 3,973,725 | 8/1976 | Watanabe et al. | 235/151.3 X |

Primary Examiner—Edward J. Wise
Attorney, Agent, or Firm—Robert P. Cogan; Timothy L. Burgess

[57] ABSTRACT

Apparatus and method are provided for determining mean corpuscular volume of cells in a sample passing through a conductivity cell. A coincidence corrected red blood cell count is generated by conventional means, and a signal indicative of hematocrit level is provided. A digital representation of the corrected red blood cell count is loaded into a register connected to comparator means. A digital output generated in response to the hematocrit level indicated by the hematocrit signal is utilized as a clock pulse train. The clock pulse train has a total length indicative of the hematocrit level, or a multiple thereof. The count indicated by the clock pulse train is compared by the comparator means, which acts as a divider, to the red blood cell count. The output of the comparator means comprises a digital number which is indicative of the mean corpuscular volume of a sample.

13 Claims, 1 Drawing Figure

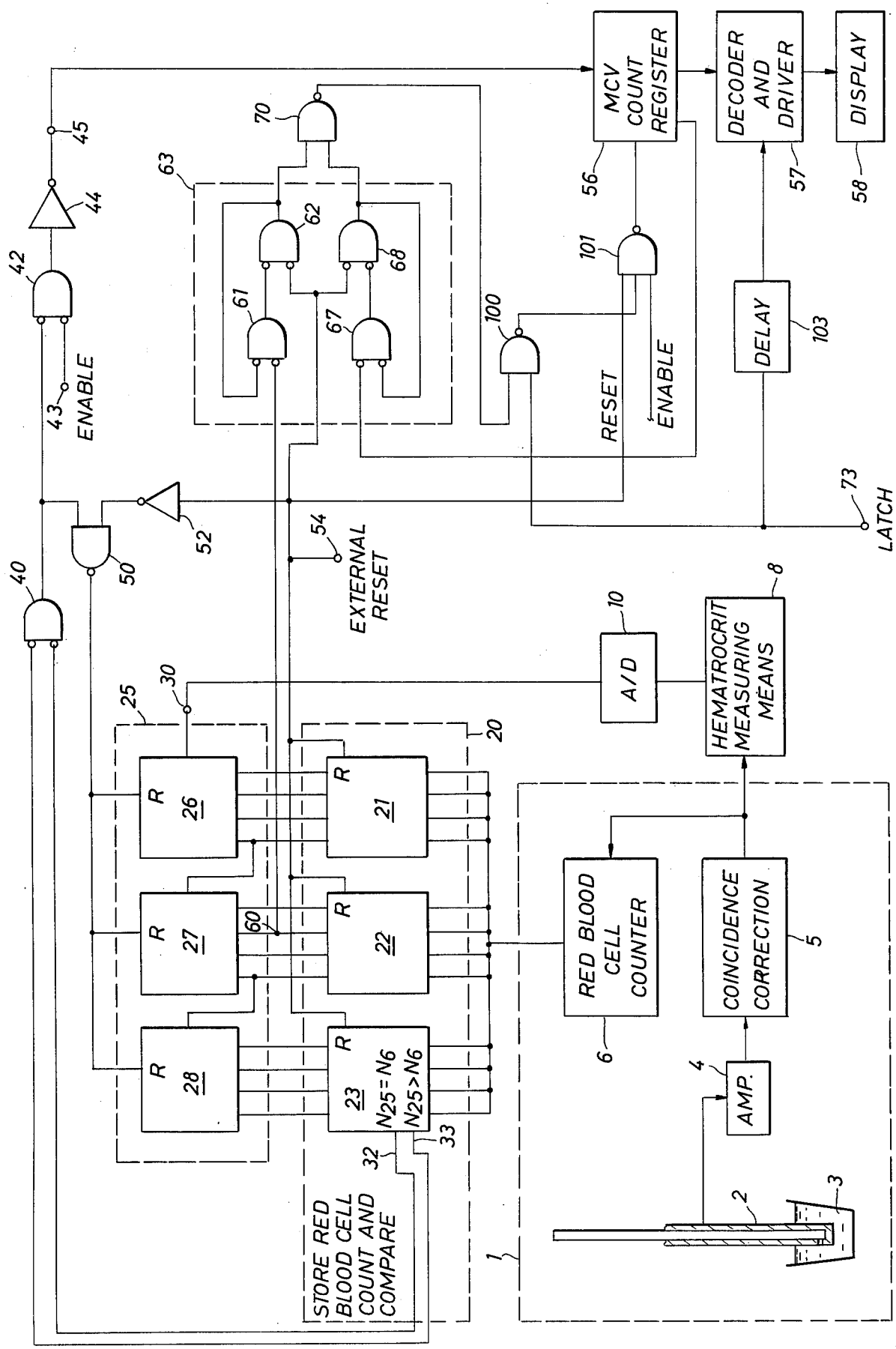

MEAN CORPUSCULAR VOLUME MEASURING APPARATUS AND METHOD

BACKGROUND OF THE INVENTION

1. Field of Invention

The present invention relates to means for electrical measurement of hematological parameters, and more particularly to means for providing an indication of mean corpuscular volume of blood cells in a diluted sample.

2. Description of the Prior Art

Mean corpuscular volume refers to the average size of red blood cells in a blood sample. The context comtemplated for the present invention is a blood cell counter using a conductivity sensor, having an aperture through which a diluted blood sample is passed, and having electrodes on either side of the aperture. Sensor pulses are produced indicative of the number of blood cells in the sample passing through the aperture. An example of such an apparatus is disclosed in U.S. Pat. No. 3,921,066, issued to Angel, et al. on Nov. 18, 1975, now owned by the assignee herein, the disclosure of which is incorporated herein by reference. The context further contemplated is an apparatus in which measurement of the hematocrit of the blood sample is made. Hematocrit is the percentage of red blood cell volume out of the entire volume of a blood sample. Examples of hematocrit measuring apparatus are found in U.S. Pat. No. 3,828,260, issued to Underwood on Aug. 6, 1974, and now owned by the assignee herein, and co-pending commonly assigned patent application Ser. No. 725,268, filed Sept. 21, 1976, also assigned to the assignee herein.

Prior circuits have been provided for deriving outputs indicative of mean corpuscular volume including discriminating circuitry for segregating sensor output pulses within ranges of magnitude and providing an averaging calculation. Such arrangements are not only rather cumbersome, but may be subject to error as being based on non-coincidence corrected red blood cell counts.

SUMMARY OF THE INVENTION

It is therefore an object of the present invention to provide a method and apparatus for providing an output indicative of means corpuscular volume of a diluted blood sample based on a coincidence-corrected red blood cell count and a hematocrit measurement.

It is another object of the present invention to provide apparatus for computing mean corpuscular volume particularly suited for construction in digital embodiments.

Briefly stated, in accordance with the present invention, there is provided a method and apparatus for providing an output indicative of mean corpuscular volume in which a coincidence corrected red blood cell count is provided to register means, and a hematocrit measurement is utilized for production of a pulse train having a total length corresponding to a level of hematocrit measured for the sample, or a multiple thereof. The pulse train is used to clock a counter and divider means which provides one output pulse for every preselected number of input pulses thereto, the preselected number being determined by the count set in the register means. The total number of output pulses comprises a digital number indicative of mean corpuscular volume. In a further form, control circuit terminals may be connected to respond to selected significant digits of a register reading indicative of mean corpuscular volume, or to the digital representation of the coincidence corrected red blood cell count for controlling control circuitry to inhibit the production of an output signal when the red blood cell count or mean corpuscular volume level are below value corresponding to the selected significant digits.

BRIEF DESCRIPTION OF THE DRAWINGS

The means by which the foregoing objects and features of invention are achieved are pointed out with particularity in the claims forming the concluding portion of the specification. The invention, both as to its organization and manner of operation, may be further understood by reference to the following FIGURE, taken in connection with the following description.

The FIGURE is a schematic representation of a means for determining mean corpuscular volume constructed in accordance with the present invention.

DESCRIPTION OF THE PREFERRED EMBODIMENT

Referring to the FIGURE, there is illustrated an apparatus for determining mean corpuscular volume constructed in accordance with the present invention. Measuring apparatus 1 is provided which may comprise, for example, the apparatus of the above-cited patent to Angel, et al. The measuring apparatus 1 includes a well-known conductivity sensor 2 for measuring blood cells in a blood dilution sample 3 and providing an uncorrected red blood cell count to a buffer amplifier 4. The amplifier 4 provides an output to coincidence correction circuitry 5 for producing a coincidence-corrected red blood cell count. Coincidence correction is correction for the passage of more than one blood cell passing at one time through the aperture in the sensor 2 and resolved by one sensor pulse as one blood cell. The more dense the dilution of the red blood cell sample, the greater the occurrence of coincidence and the need for correction. Coincidence circuitry is well-known in the art. In the preferred embodiment, the sample 3 is a 160,000 to 1 dilution, requiring only the order of 3 to 4 percent coincidence correction for red blood cell counts within normal ranges. The coincidence correction circuit 5 provides an output to counting circuitry 6 which comprises well-known digital counting and encoding means for providing an output indicative of the red blood cell count for a particular sample 3. Well-known means such as described in the above-cited patent to Angel et al., control the passing of a predetermined sample volume through the aperture in the sensor 2.

The amplifier 4 also provides output pulses to a hematocrit calculation means 8. The hematocrit calculation means 8 is preferably of the type which self-corrects for coincidence with a non-coincidence corrected input. An example of a hematocrit calculation means 8 is found in the above-cited references and in copending, commonly assigned patent application Ser. No. 725,268.

In the preferred embodiment, the hematocrit measuring apparatus provides an analog indication of hematocrit level. The hematocrit measuring apparatus has its output connected to an analog to digital converter 10. The analog to digital converter 10 is selected to provide an output pulse train having a length indicative of the analog output level of the measuring apparatus 8, or a multiple thereof. The pulse repetition rate compatible with operating characteristics of components further described below. In the present embodiment, the analog to digital converter 10 is connected to provide a pulse train length equal to 100 times the digital representation of the hematocrit level in the context of the register and the display circuitry used. The expected range of possible hematocrit levels is zero to sixty percent, and output levels are normalized accordingly.

In the present embodiment, the counter 6 provides a binary coded decimal output of three digits. Each digit has four significant bits. The counter 6 output is calibrated to be capable of indicating 0 through 9.99 million cells per cubic millimeter. The output of the counter 6 is connected to a magnitude comparator 20 having stages 21, 22 and 23, each comparing four bits. A single output line from the comparator 6 is illustrated only for simpliticy in the FIGURES. Each of the stages 21-23 respectively represent comparisons of the least significant, second significant and most significant digits of the number represented by the count in the counter 6.

A counter 25 is provided having first, second and third stages 26, 27 and 28, each respectively connected to a comparison terminal of one of the stages 21, 22 and 23. The stages 26, 27 and 28 are interconnected by interconnection means such that they act as a counter which is clocked by an input at a clock terminal 30. The stages of the counter 25 and magnitude comparator 20 are interconnected so that each bit position in the register 25 overflows and the next bit position begins counting when a count in the register 25 equals the count in a corresponding bit postiion in the register 6. Consequently, the clock input at the clock terminal 30 incredments the count in the stages of the register 25, until the count therein equals the count in the register 6. When this condition occurs, the stage 23 of magnitude comparator 20 provides a count out signal at an output terminal 32. In order to provide for reliability, an additional terminal 33 is provided if for some reason such an interbit jitter or otherwise, the output pulse at the terminal 32 is missed when the counts are equal. The output terminal 33 provides a pulse when the count in the counter 25 is greater than the register 6. The mangitude comparator 20 thus also comprises dividing means. The above described operation may be embodied by well-known components. For example, the stages 26, 27 and 28 may each be embodied by an RCA 4518 microcircuit chip. The stages 21, 22 and 23 may each be embodied by an RCA 4585 microcircuit chip which comprises register and digital comparator stages.

The oututs of the terminal 32 and 33 are connected to a NOR gate 40. An output at either the terminal 32 or 33 will cause a stage change at the output of the NOR gate 40. The output of the NOR gate 40 is connected to a first input of a NOR gate 42, having a second input terminal 43 controlled by a control terminal for enabling or disabling an output therefrom. The other input to the NOR gate 40 may for example, comprise an enabling signal controlled by a function selection switch (not shown) included in the apparatus 1 described above. The output of the NOR gate 42 is connected by an inverter 44, which acts as a buffer, to an output terminal 45. Thus when a count in the counter 25 reaches the preselected level in the register 6, an output count is provided at the output count terminal 45.

The output of NOR gate 40 is also connected to a first input of a NAND gate 50, having its output connected to reset terminals of the stages 26, 27 and 28. The NAND gate 50 has another input terminal, coupled through an inverter 52, to an external reset terminal 54 for resetting both the register 20 and counter 25 at the completion of a mean corpuscular volume measurement. The external reset terminal may be controlled by function selection circuitry (not shown) also within the apparatus 1 described above.

Thus when an output pulse is provided from either the terminal 32 or 33, one mean corpuscular volume unit increment is provided at the count output terminal 45, and the register 25 is reset so that the process may be repeated. This process is repeated until the total length of the pulse train output of the analog to digital converter 10 has been used to clock the counter 25. At the end of a count, a partial remainder will be left in the counter 25 and remain there until external reset is provided. Since a clock rate equal to one hundred times the hematocrit level has been provided, precision of the output produced at the count output terminal 45 is not affected within tolerances determined by resolution of the measuring apparatus 1.

The output terminal 45 is connected to a mean corpuscular volume count register 56 which provides an output to decoder and display driver means 57. A conventional display means 58 is connected to the decoder and display driver means 57 for providing a display indicated by the digital number supplied to the mean corpuscular volume count register 56.

It may occur in the hematological measurements that either a red blood cell level or a hematocrit level of a sample will be particulary low. Since the mean corpuscular volume calculation is based on these measurements, such a calculation based on exceedingly low levels will be lacking in precision and reliability. Therefore, further in accordance with the present invention, means are provided for disabling a mean corpuscular volume calculation, should undesired conditions be present for a meaningful mean corpuscular volume reading. Means are provided for responding to preselected levels of red blood cell or mean corpuscular volume readings. For example, in a typical embodiment, it is desired to disable the provision of a mean corpuscular volume output when the red blood reading is less than 0.20 million cells per cubic millimeter. Therefore, a control terminal 60 is connected to the output terminal representing the second significant bit of the second significant digit of the red blood cell count represented in the register 25. The counter 25 counts up to a count equal to a count in the counter 6 to perform division. This output is available at a more convenient time to use. The control terminal 60 is connected to a set terminal of a flip-flop comprised of first and second NOR gates 61 and 62. In the condition in which during a measurement and red blood cell count is below 0.20, the polarity at the terminal 60 fails to set the flip-flop 63. The reset terminal of the flip-flop 66 comprised of first and second NOR gates 67 and 68, is provided having a set terminal connected to a terminal representing the third significant bit of the second significant digit in the mean corpuscular volume count register 56. In this manner, a signal is not provided at the set terminal of the flip-flop 56, if a resulting mean corpuscular volume rating is less than 40 cubic microns. Each of the flip-flops 63 and 66 must be set to obtain a mean corpuscular volume reading. A NAND gate 70 is connected to change state if either the flip-flop 63 or 66 is not set.

A latch signal is provided from timing means (not shown) in the apparatus 1. The latch signal is supplied to the counter register 56 via a NAND gate 100 and a NAND gate 101 and to the decoder and driver 57 via delay element 103. If at the completion of a cycle, (a latch time), both the flip-flop 63 and the flip-flop 66 are not set, the latch signal is routed via the NAND gates 100 and 101 into a reset terminal of the MCV count register 56. Since it arrives at the counters 56 before the drivers 57 due to the delay element 103, the data displayed is zero or blank until both the flip-flops 63 and 66 are set.

Summarizing the operation, at the beginning of a measurement, both the register 6 and counter 25, are reset. Control circuitry within the apparatus 1 produces the red blood cell count and hematocrit reading provided by the counter 6 and hematocrit measuring apparatus 8 respectively. Enabling circuitry (not shown) enables the provision of the pulse train from the analog to digital converter 10 to the clock terminal of the counter 25. This operation continues during performance of a red blood cell count. A pulse train is produced and the output terminal 45 which is indicative of the hematocrit reading divided by the red blood cell count, and therefore is representative of mean corpuscular volume. This pulse train is provided to the mean corpuscular volume count register 56 which includes appropriate scaling circuitry. Desired stages of the registers 25 and 56 are monitored so that a provision of a meaningless mean corpuscular volume output is inhibited. Many modifications may be made in the particular circuit disclosed to provide mean corpuscular volume measuring apparatus constructed in accordance with the present invention. Other forms of counting and comparison circuitry than the registers 20 and 25 may be utilized for example. Many modifications will be readily apparent to those skilled in the art.

What is claimed as new and desired to be secured by Letters Patent of the United States is:

1. Apparatus for producing a signal indicative of mean corpuscular volume of blood cells in a sample comprising: input means for supplying an input indicative of corrected red blood cell count for the sample; register means connected to said input means for storing an indication of said corrected red blood cell count; counter means; clock source means providing a pulse train having a length indicative of a hematocrit measurement made of said sample; means connecting said clock source means to a clock terminal of said counter means; interconnection means interconnecting said counter means and said register means for providing one output pulse for a preselected number of clock pulses, the preselected number being determined by the indications stored in said register means, whereby the number of output pulses is indicative of mean corpuscular volume for the sample.

2. Apparatus according to claim 1 further comprising controlled switching means connected between said register means and said counter means for resetting said counter means in response to each output pulse.

3. Apparatus according to claim 2 wherein said input means comprises an analog to digital converter for connection to hematocrit measuring apparatus providing an analog output.

4. Apparatus according to claim 3 wherein said interconnection means and said register means comprise a digital comparator.

5. Apparatus according to claim 4 further comprising a mean corpuscular volume count register connected for receiving said output pulses, whereby a digital number is set in said mean corpuscular volume count register in response to the output pulses indicative of mean corpuscular volume.

6. Apparatus according to claim 5 further comprising decoder and display driver means coupled to the output of said mean corpuscular volume count register and display means connected to the output of said decoder and driver means.

7. Apparatus according to claim 6 further comprising control switching means connected to a terminal indicative of a preselected bit of a preselected digit in one of said register for providing an output connected for disabling said display means when a count in said register is below the preselected level determined by the terminal.

8. Apparatus according to claim 6 further comprising first and second control switching each connected to one register terminal indicative of preselected levels of stored counts of mean corpuscular volume and corrected red blood cell count and each having outputs connected for disabling said display means when said mean corpuscular volume or corrected red blood cell count is below a predetermined level, whereby display of unreliable values of mean corpuscular volume is inhibited.

9. A method for providing an indication having a value indicative of mean corpuscular volume comprising the steps of: setting a value indicative of a corrected red blood cell count in a register; providing an indication of hematocrit level and converting said indication into a pulse train having a total length indicative of a hematocrit level for the sample; providing the pulse train to a counter; and producing an output pulse train for every preselected number of pulse train pulses, the preselected number being determined by the setting in said register.

10. The method of claim 9 further comprising the step of providing the output pulses to a mean corpuscular volume count register, whereby an indication of mean corpuscular volume is provided.

11. The method of claim 15 further comprising providing the output of said mean corpuscular volume count register to utilization means.

12. The method according to claim 11 further comprising the step of disabling said utilization means when a number in one of said registers is below a preselected level.

13. Apparatus for continually indicating mean corpuscular volume for a sample while a red blood count is in process comprising: means for registering an instantaneous red blood cell count provided from a source for providing a count indicative of coincidence corrected red blood cell count, means for registering totalized volume of cells in the sample, and dividing means coupled to both of said registering means for providing an output indicative of an instantaneous value of mean corpuscular volume.

* * * * *